(12) United States Patent
Ramsteiner

(10) Patent No.: US 10,551,324 B2
(45) Date of Patent: Feb. 4, 2020

(54) DEVICE AND METHOD FOR CHECKING WINDSHIELD WIPER BLADES

(71) Applicant: Robert Bosch GmbH, Stuttgart (DE)

(72) Inventor: Ingo Ramsteiner, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 258 days.

(21) Appl. No.: 15/319,033

(22) PCT Filed: May 8, 2015

(86) PCT No.: PCT/EP2015/060198
§ 371 (c)(1),
(2) Date: Dec. 15, 2016

(87) PCT Pub. No.: WO2015/197253
PCT Pub. Date: Dec. 30, 2015

(65) Prior Publication Data
US 2017/0138865 A1    May 18, 2017

(30) Foreign Application Priority Data
Jun. 27, 2014   (DE) .................. 10 2014 212 500

(51) Int. Cl.
*G01N 21/88* (2006.01)
*G01B 11/30* (2006.01)
(Continued)

(52) U.S. Cl.
CPC ....... *G01N 21/8803* (2013.01); *G01B 11/306* (2013.01); *G01M 99/008* (2013.01); *B60S 1/38* (2013.01); *B60S 2001/3844* (2013.01)

(58) Field of Classification Search
CPC . G01N 21/8803; G01N 21/84; G01M 99/008; G01M 11/00; G01B 11/306;
(Continued)

(56) References Cited

U.S. PATENT DOCUMENTS 5,796,487 A    8/1998   Guerra
8,077,929 B2 * 12/2011  Heidt ................ G06K 9/00046
                                                        356/71

FOREIGN PATENT DOCUMENTS

CN    1984802 A    6/2007
CN    202306586 U  7/2012
GB    2056059 A    3/1981

OTHER PUBLICATIONS

International Search Report dated Jul. 31, 2015, of the corresponding International Application PCT/EP2015/060198 filed May 8, 2015.

* cited by examiner

*Primary Examiner* — Kara E. Geisel
*Assistant Examiner* — Amanda Merlino
(74) *Attorney, Agent, or Firm* — Norton Rose Fulbright US LLP; Gerard A. Messina

(57) ABSTRACT

A device for checking a windshield wiper blade of a motor vehicle, includes an at least partially transparent body having a contact side which is designed for contacting with the windshield wiper blade to be checked; a light-incidence side which is designed to allow light to enter into the body; and a light-exit side. The at least partially transparent body is designed in such a way that light entering the body through the light-incidence side is reflected at least partially at the contact side, and reflected light exits the body through the light-exit side.

10 Claims, 1 Drawing Sheet

(51) Int. Cl.
*G01M 99/00* (2011.01)
*B60S 1/38* (2006.01)

(58) Field of Classification Search
CPC ... G01B 5/207; G01B 5/20; B60S 1/38; B60S 2001/3844
See application file for complete search history.

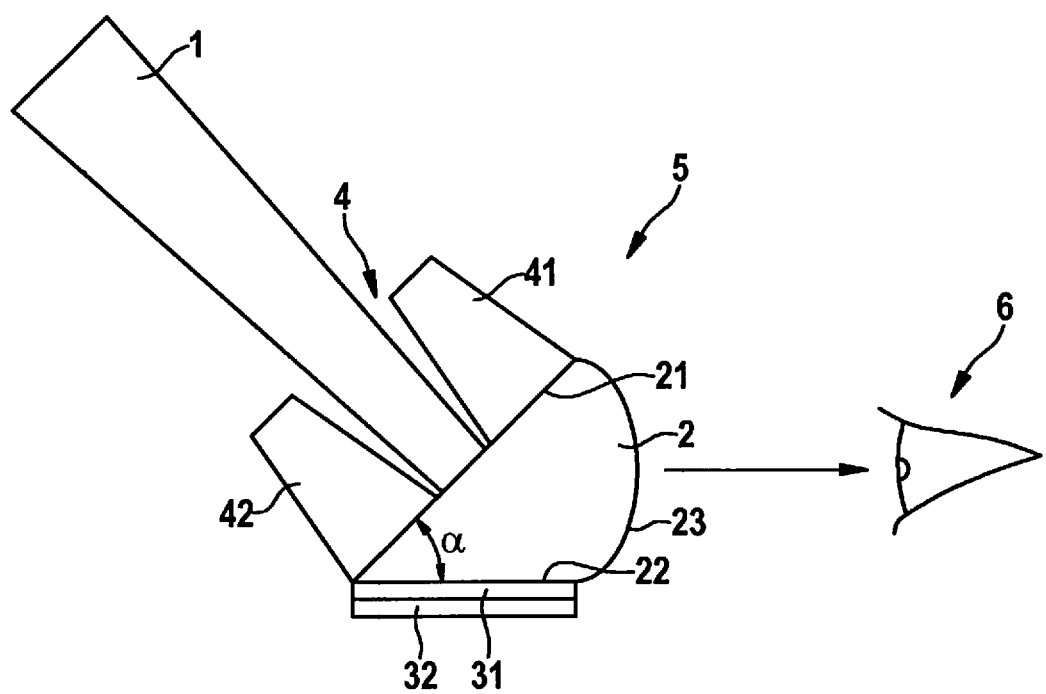

DEVICE AND METHOD FOR CHECKING WINDSHIELD WIPER BLADES

FIELD

The present invention relates to a device and a method for checking windshield wiper blades, especially for checking windshield wiper blades for motor vehicles.

BACKGROUND INFORMATION

Windshield wiper blades (wiper blades) are parts subject to wear; in the course of time, uneven places develop on the wiper blade owing to mechanical stress. Because of this, streaks come about during wiping, which may obscure driver visibility considerably, and therefore lead to hazards in road traffic.

The condition of the wiper blade and sight obscuration, caused by wear, under unfavorable weather and lighting conditions are difficult to demonstrate in the service station. A need for replacement may be difficult to convey to the customer through a visual inspection or by feeling the wiper blade itself. Also, looking at the windshield after the actuation of the windshield washer system, because of the clean washer fluid and the favorable light conditions at the service reception, which generally takes place in a building interior or at least in a sheltered area, does not convey a correct impression as to how poor the visibility would be, for example, in the case of salty splash water and/or sunlight exposure, especially in the case of light from oncoming traffic.

Therefore, an object of the present invention is to provide a device and a method which make it possible to check the condition of a windshield wiper blade quickly and in a manner transparent for the customer.

SUMMARY

A device for checking a wiper blade, especially of a motor vehicle, is characterized in that the device includes a body which is made at least partially of a transparent material, e.g., glass or a plastic such as polymethyl methacrylate or polycarbonate, for example.

The body has a contact side which is designed for contacting with the wiper blade to be checked; a light-incidence side which is designed to allow light to enter into the body; and a light-exit side. The body is designed in such a way that light entering the body through the light-incidence side is reflected at least partially at the contact surface, and reflected light exits the body through the light-exit side.

A method according to the present invention for checking a wiper blade, especially a windshield wiper blade of a motor vehicle, includes the following steps:
  Placing the wiper blade to be checked on a contact side of an at least partially transparent body;
  Causing light to enter into the at least partially transparent body;
  Observing light that has entered the at least partially transparent body, been reflected at least partially at the contact surface and exited from the body through a light-exit side.

The configuration of the elements indicated and the cross-sectional profile of the at least partially transparent body are such that light entering the body through the light-incidence side, after total reflection at the contact side, emerges through the light-exit side of the body.

The observer views the device from the light-exit side. Because of the light entering through the light-incidence side, he will perceive the image of the light-incidence side reflected at the contact side as brightness. At the places at which the material of the wiper blade is in direct contact with the contact side, the total reflection is prevented. Therefore, these areas seem dark or black to the observer.

If a wiper blade is undamaged, the observer therefore sees a continuous black strip when looking at the light exiting from the body.

If the wiper blade is locally damaged, the contact is impaired at the location in question, which means total reflection again occurs that allows the damaged location to become visible as bright interruption of the black contact line. In this way, damage and wear of the wiper blade may be recognized quickly and clearly, and demonstrated very vividly to the customer.

In one specific embodiment, the light-incidence side has a roughened surface that causes diffuse scattering of the incoming light, and in this way permits a very uniform illumination, in which damage to the wiper blade may be recognized particularly clearly. Alternatively or additionally, the light-incidence side may be coated with a matte, light-scattering color in order to achieve uniform illumination.

In one specific embodiment, the light-incidence side is coated with a fluorescent color which, especially in response to illumination with natural or artificial UV-light, generates homogeneous light in a desired wave range that is predefined by the properties of the fluorescent color.

In one specific embodiment, in addition, the device has an artificial light source which is designed to radiate light onto the light-incidence side, in order to produce a uniform illumination. Thus, the device is able to be used regardless of the lighting conditions in the surrounding area. In this way, in particular, the device may also be used in dark garage spaces. Moreover, an especially homogeneous illumination may be realized with the aid of an artificial light source.

Among other things, incandescent bulbs, LEDs, especially LED films, gas-discharge lamps and/or TFT lighting elements may be used as light source.

In particular, the light source may be formed as a planar light source along the light-incidence side of the body, in order to bring about an optimal, especially homogeneous illumination.

In one specific embodiment, the light-exit side is curved in such a way that it forms a converging lens, particularly a cylindrical converging lens, which acts like a magnifier and furnishes the observer with an enlarged image of the contact point between the body and the wiper blade. Alternatively, the light-exit side may be formed with a Fresnel lens acting as converging lens. In particular, even small damages of the wiper blade may be recognized very well through a magnifying converging lens.

In one specific embodiment, the body is formed as a strip which has a length, and a width and height markedly smaller in comparison to the length. The strip is preferably at least as long as the longest wiper blade to be checked. In this way, the wiper blade is able to be checked over its entire length in a single step, and it is not necessary to position the wiper blade repeatedly on the contact surface.

On the contact surface, at least one guide rail may be formed, which is provided to guide the wiper blade in order to assist the user to correctly position the wiper blade on the contact surface. In particular, two mutually parallel guide rails may be provided, between which a gap is formed for receiving the wiper blade.

Such a guidance of the wiper blade on the contact surface is especially useful if, as described above, the light-exit side is formed as a lens, since the image-forming properties of the lens are optimized for a predefined position of the wiper blade on the contact surface. Moreover, the guide rails are able to protect the contact surface from scratching.

The guide rails may be components made of plastic or rubber that are mounted, especially stuck onto the body. Alternatively, the guide rails may be an integral part of the body produced, for example, by extrusion.

BRIEF DESCRIPTION OF THE DRAWING

The present invention is explained in greater detail with reference to the FIGURE.

The FIGURE shows a cross-section of an example device in accordance with the present invention.

DETAILED DESCRIPTION OF EXAMPLE EMBODIMENTS

The FIGURE shows a cross-section through an exemplary embodiment of a device 5 according to the present invention. Device 5 has a body 2 which is formed as a strip, the longitudinal direction of the strip extending perpendicular to the drawing plane of the FIGURE. Body 2 is formed at least partially from an optically transparent material, e.g., glass or a transparent plastic such as polymethyl methacrylate or polycarbonate, for example.

In the representation in the FIGURE, body 2 has a light-incidence side 22 running horizontally in its lower area, and a contact side 21 running at an acute angle α with respect to light-incidence side 22, so that in the cross-sectional view shown in the FIGURE, light-incidence side 22 and contact side 21 form the sides of a triangle. The ends of the two sides are joined to each other by a light-exit side 23, which is curved in the exemplary embodiment shown in the FIGURE, so that body 2 has two flat sides 21, 22 and one curved side 23 that lies opposite the corner at which the two flat sides 21, 22 adjoin each other.

On light incidence side 22, a fluorescent coating 31 and a planar illumination device 32 are provided, which bring about a homogeneous light falling through light-incidence side 22 during operation.

A wiper blade 1 to be checked is placed with its face on flat contact side 21 of body 2. Two guide rails 41, 42, which run parallel to the longitudinal extension of body 2, form a gap 4 between them that receives wiper blade 1, and assists and facilitates the correct positioning of wiper blade 1 on the contact side.

Body 2 is designed in such a way that the light generated on light-incidence side 22, after total reflection at contact side 21, exits through light-exit side 23 of body 2. An observer/user 6 who is employing device 5 in order to check wiper blade 1, observes light-exit side 23 of body 2. He sees the image of light-incidence side 22, reflected at contact side 21, as bright area. Since the material of wiper blade 1 has a different optical refractive index than air, no total reflection occurs at the places where the material of wiper blade 1 touches contact side 21. Therefore, these areas appear dark or black to observer 6.

There is no contact between wiper blade 1 and contact side 21 at places where wiper blade 1 is damaged. At these places, the light is (totally) reflected at the interface between contact side 21 and the surrounding air, and in the image perceived by observer 6, the damaged places become visible as bright interruptions in the black contact line. In this way, damage and wear of wiper blade 1 may be recognized quickly and clearly, and demonstrated vividly to the customer.

What is claimed is:

1. A device for checking a windshield wiper blade of a motor vehicle, comprising:
   at least partially transparent body, the body having:
      a contact side designed for contacting with the wiper blade to be checked;
      a light-incidence side designed to allow light to enter into the body; and a light-exit side;
   wherein the body is designed in such a way that light entering the body through the light-incidence side is reflected at least partially at the contact side, and reflected light exits the body through the light-exit side, wherein the light incidence side and the contact side are arranged at an acute angle with respect to one another, the light exit side connecting ends of the light incidence side and the contact side, and
   wherein at least one guide rail for guiding the wiper blade is formed on the contact side.

2. The device as recited in claim 1, wherein the light-incidence side has a roughened surface.

3. The device as recited in claim 1, wherein the light-incidence side is coated with at least one of a matte color, light-scattering color, and fluorescent color.

4. The device as recited in claim 1, wherein the device additionally has at least one light source, which is designed to radiate light onto the light-incidence side.

5. The device as recited in claim 4, wherein the light source is a UV light source.

6. The device as recited in claim 4, wherein the light source is formed as a planar light source along the light-incidence side of the body.

7. The device as recited in claim 1, wherein the light-exit side is a magnifying converging lens.

8. The device as recited in claim 1, wherein the light-exit side is a magnifying converging lens, the lens being one of a cylindrical converging lens or a Fresnel lens.

9. The device as recited in claim 1, wherein the body is formed as a strip.

10. A method for checking a windshield wiper blade of a motor vehicle, comprising:
    placing the wiper blade to be checked on a contact side of an at least partially transparent body;
    causing light to enter into the body; and
    observing light that has entered into the body, reflected at least partially at the contact side, and exited from the body, wherein a light incidence side of the body and the contact side are arranged at an acute angle with respect to one another, and wherein a light exit side of the body connects ends of the light incidence side and the contact side.

* * * * *